United States Patent
Bischoff et al.

(10) Patent No.: US 11,207,313 B2
(45) Date of Patent: Dec. 28, 2021

(54) PHARMACEUTICAL COMPOSITION (71) Applicant: Novartis AG, Basel (CH)

(72) Inventors: Claus Dieter Bischoff, Basel (CH); Sonali Bose, East Hanover, NJ (US); Geoffrey Gogniat, Basel (CH)

(73) Assignee: Novartis AG, Basel (CH)

( * ) Notice: Subject to any disclaimer, the term of this patent is extended or adjusted under 35 U.S.C. 154(b) by 11 days.

(21) Appl. No.: 16/125,809

(22) Filed: Sep. 10, 2018

(65) Prior Publication Data
US 2019/0076418 A1   Mar. 14, 2019

Related U.S. Application Data (60) Provisional application No. 62/557,298, filed on Sep. 12, 2017.

(51) Int. Cl.
| | |
|---|---|
| *A61K 31/46* | (2006.01) |
| *A61K 9/48* | (2006.01) |
| *A61P 1/16* | (2006.01) |
| *A61K 9/08* | (2006.01) |
| *A61K 47/14* | (2017.01) |

(52) U.S. Cl.
CPC ............ *A61K 31/46* (2013.01); *A61K 9/08* (2013.01); *A61K 9/4825* (2013.01); *A61K 9/4858* (2013.01); *A61K 9/4866* (2013.01); *A61K 47/14* (2013.01); *A61P 1/16* (2018.01); *A61K 9/4833* (2013.01)

(58) Field of Classification Search
CPC ........ A61K 31/46; A61K 9/08; A61K 9/4825; A61K 9/4858; A61K 9/4866; A61K 47/14; A61K 9/4833; A61P 1/16
See application file for complete search history.

(56) References Cited

U.S. PATENT DOCUMENTS

| | | | | |
|---|---|---|---|---|
| 2006/0252670 A1 | 11/2006 | Fiorucci et al. | | |
| 2012/0270931 A1* | 10/2012 | Sherman | ............... | A61K 47/14 514/456 |
| 2014/0005123 A1* | 1/2014 | Goncalves | ............. | A61K 9/107 514/20.5 |

FOREIGN PATENT DOCUMENTS

| | | | |
|---|---|---|---|
| WO | WO2012/087519 A1 | 6/2012 | |
| WO | WO-2012087519 A1 * | 6/2012 | ............... A61P 3/04 |
| WO | 2017/145031 A1 | 8/2017 | |
| WO | 2017/145040 A1 | 8/2017 | |
| WO | 2017/145041 A1 | 8/2017 | |
| WO | WO2018/039384 A1 | 3/2018 | |
| WO | WO2018/183193 A1 | 10/2018 | |

OTHER PUBLICATIONS

Maniruzzaman et al (Year: 2012).*
PubChem CID 6435912 (Year: 2006).*
Clinical Trials.gov Identifier NCT02516605 (Year: 2015).*
PubChem CID 121418176 (Year: 2016).*
Ku etal (Year: 2010).*

* cited by examiner

*Primary Examiner* — Jeffrey S Lundgren
*Assistant Examiner* — Ibrahim D Bori
(74) *Attorney, Agent, or Firm* — Emily T. Wu (57) ABSTRACT

The present invention relates to a pharmaceutical composition for oral administration comprising a non-bile farnesoid X receptor (FXR) agonist 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient; to a capsule for oral administration comprising said pharmaceutical composition; to the use of said pharmaceutical composition for the treatment of a FXR mediated disorder or condition; and to a process for preparing said pharmaceutical composition.

10 Claims, 2 Drawing Sheets

Figure 1   Dog Plasma profiles in fasted conditions (normalized to 5 µg/kg)

Figure 2    Pharmacokinetics (PK) in fed dogs

PHARMACEUTICAL COMPOSITION

FIELD OF THE DISCLOSURE

The present invention relates to the field of pharmacy, particularly to a pharmaceutical composition for oral administration comprising non-bile farnesoid X receptor (FXR) agonist and at least one lipid excipient. Specifically, the disclosure relates to a pharmaceutical composition for oral administration comprising 2-[(1R,3R,5S)-3-({5-cyclopropyl-3-[2-(trifluoromethoxy) phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient; to a capsule for oral administration comprising said pharmaceutical composition; to the use of said pharmaceutical composition for the treatment of a FXR mediated disorder or condition; to the use of said pharmaceutical composition in the manufacture of a medicament; and to a process for preparing said pharmaceutical composition.

BACKGROUND OF THE DISCLOSURE

Nuclear receptors constitute a superfamily of transcriptional regulatory proteins that share structural and functional properties and function as receptors for example steroids, retinoids, vitamin D, and thyroid hormones (Evans et al. Science 1988, 240, 889). The farnesoid X receptor (FXR) is a member of the nuclear hormone receptor superfamily and is primarily expressed in the liver, kidney and intestine (Seol et al. *Mol. Endocrinol.* 1995, 9, 72-85; Forman et al. *Cell* 1995, 81, 687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (Makishima et al. *Science* 1999, 284, 1362-1365; Parks et al. *Science* 1999, 284, 1365-1368; Wang et al. *Mol. Cell.* 1999, 3, 543-553), which serve to inhibit cholesterol catabolism (Urizar et al. *J. Biol. Chem.* 2000, 275, 39313-39317).

The specific non-bile FXR agonist 2-[(1R,3R,55)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, may be used for the treatment of an FXR mediated disease or disorder. The compound and its preparation are disclosed in WO 2012/087519 (herein included by reference). There is a need to provide a commercially viable pharmaceutical composition comprising non-bile FXR agonist, such as 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof.

SUMMARY OF THE DISCLOSURE

The design of a pharmaceutical composition, a pharmaceutical dosage form, as well as a commercially viable process to prepare the pharmaceutical composition, for a non-bile FXR agonist, such as 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, is especially challenging. This non-bile FXR agonist is a highly potent active pharmaceutical ingredient (API) classified by the biopharmaceutics classification system as a class IV compound, e.g. highly hazardous compound. This non-bile FXR agonist is difficult to formulate due to its physiochemical properties, its high potency and finding a suitable pharmaceutical composition, in a reliable and robust way, proved challenging. For example, due to its very high potency a low dosage is needed, generating unwanted formulation issues such as content uniformity, and additional handling restrictions on a large manufacturing scale. Furthermore, this non-bile FXR agonist has a low water solubility and mixture of the compound with conventional excipients proved difficult (instability, unpredictable dissolution rates, irregular bioavailability). Accordingly, a suitable and robust solid pharmaceutical composition overcoming the above problems needs to be developed.

In view of the above-mentioned difficulties, and considerations, it was surprising to find a stable pharmaceutical composition that allows handling low amount of the active compound, thus avoiding any content uniformity or manufacturing issues.

In one aspect, the present invention relates to a pharmaceutical composition for oral administration comprising a non-bile FXR agonist, such as 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient.

Aspects, advantageous features and preferred embodiments of the present invention summarized in the following items, respectively alone or in combination, contribute to solving the object of the invention.

Item A1. A pharmaceutical composition for oral administration comprising a non-bile FXR agonist and at least one lipid excipient.

Item A2. A pharmaceutical composition for oral administration comprising 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient.

Item A3. The pharmaceutical composition according to item A1 or A2, wherein the lipid excipient is selected from propylene glycol esters of fatty acids, triglycerides or mixed glycerides, or mixtures thereof.

Item A4. The pharmaceutical composition according to items A1 to A3, wherein the lipid excipient is selected from glycerol mono/dicaprylate, glyceryl caprylate/caprate, propylene glycol monolaurate, or mixtures thereof.

Item A5. The pharmaceutical composition according to any one of items A1 to A4, wherein the pharmaceutical composition further comprises a surfactant, preferably with a hydrophilic-lipophilic balance inferior at 12.

Item A6. The pharmaceutical composition according to item A5, wherein the surfactant is selected from polyoxyethylene (25)-glyceryl trioleate, polyoxyethylene (20) glyceryl trioleate, polyoxyethylene (20) sorbitan trioleate, caprylic/capric triglyceride, or mixtures thereof.

Item A7. The pharmaceutical composition according to any one of items A1 to A4, wherein the pharmaceutical composition further comprises a surfactant with a hydrophilic-lipophilic balance superior at 12 and optionally a co-solvent.

Item A8. The pharmaceutical composition according to item A7, wherein the surfactant is selected from polyoxyl 40 hydrogenated castor oil, polyoxyl 60 hydrogenated castor, oil alkyl ether ethoxylate, cetostearyl alcohol ethoxylate, polyethylene glycosylated mixed glycerides, macrogolglycerol ricinoleate, polysorbates, sorbitan trioleate, or mixtures thereof.

Item A9. The pharmaceutical composition according to item A7 or A8, wherein the co-solvent is selected from ethanol, glycerol, polyethylene glycol, glycofurol, transcutol, propylene glycol, or mixtures thereof.

Item A9a. The pharmaceutical composition according to any item A2 to A9, wherein pharmaceutical composition comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof in an amount of about 0.001% to about 0.04% by weight of the composition, in an amount of about 0.002% to about 0.04% by weight of the composition, or in an amount of about 0.005% to about 0.035% by weight of the composition.

Item A9b. The pharmaceutical composition according to item A9a, wherein pharmaceutical composition further comprises at least one lipid excipient.

Item A9c. The pharmaceutical composition according to item A9b, wherein pharmaceutical composition comprises at least one lipid excipient in an amount of about 99.998% to about 99.96% by weight of the composition, or in an amount of about 99.995% to about 99.965% by weight of the composition.

Item A9d. The pharmaceutical composition according to any item A9c, wherein the lipid excipient is selected from propylene glycol esters of fatty acids, triglycerides or mixed glycerides, or mixtures thereof.

Item A9e. The pharmaceutical composition according to any item A9d, wherein the lipid excipient is selected from glycerol mono/dicaprylate, glyceryl caprylate/caprate, propylene glycol monolaurate, or mixtures thereof.

Item A10. The pharmaceutical composition according to any one of items A1 to A9e, wherein the composition is in the form of a liquid solution or a capsule, preferably a capsule.

Item A11. The pharmaceutical composition according to item A10, wherein the capsule is selected from hard shell capsule, hard gelatin capsule, soft shell capsule, soft gelatin capsule, plant-based shell capsule, or mixtures thereof.

Item A12. The pharmaceutical composition according to items A10 to A11, wherein the capsule is a gelatin capsule, or a plant-based shell capsule, preferably the capsule is a soft gelatin capsule.

Item A13. The pharmaceutical composition according to items A10 to A12, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of between about 1 to about 250 µg, e.g. about 1 to 200 µg, e.g. about 1 to 140 µg, e.g. about 1 to 120 µg.

Item A14. The pharmaceutical composition according to item A13, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of 1 µg, 5 µg, 7 µg, 10 µg, 30 µg, 50 µg, 60 µg, 90 µg, 120 µg, 140 µg, 150 µg, 200 µg, 210 µg, 220 µg, 230 µg, 240 µg, or 250 µg.

Item A15. The pharmaceutical composition according to items A13 to A14, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of about 10 µg.

Item A16. The pharmaceutical composition according to items A13 to A14, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of about 30 µg.

Item A17. The pharmaceutical composition according to items A13 to A14, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of about 90 µg.

Item A18. The pharmaceutical composition according to items A13 to A14, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of about 120 µg or about 140 µg.

Item A19. The pharmaceutical composition according to items A13 to A14, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of about 200 µg.

Item A20. The pharmaceutical composition according to items A13 to A14, wherein the capsule comprises 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, in an amount of about 210 µg, or about 220 µg, or about 230 µg, or about 240 µg, or about 250 µg.

Item A21. The pharmaceutical composition according to any one of items A1 to A20, for use as a medicine.

Item A22. The pharmaceutical composition according to any one of items A1 to A20, for use in the treatment of cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis or liver fibrosis, preferably for primary biliary cirrhosis (PBS) or non-alcoholic steatohepatitis (NASH).

Item A23. Use of the pharmaceutical composition for oral administration as defined in items A1 to A20, for the manufacture of a medicament for cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis or liver fibrosis, preferably for primary biliary cirrhosis (PBS) or non-alcoholic steatohepatitis (NASH).

Item A24. A process for preparing the pharmaceutical composition for oral administration as defined in items A1 to A20, comprising mixing a non-bile FXR agonist, preferably 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient.

Item A25. The process according to item A24, wherein the mixture is encapsulated, preferably the mixture is encapsulated in a soft gelatin capsule.

Item A26. A capsule for oral administration comprising an amount of 1 to 250 µg, or an amount of 1 to 120 µg of 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient.

Item A27. The capsule for oral administration according to item A26, wherein the lipid excipient is propylene glycol monolaurate, or glyceryl caprylate/caprate, or mixtures thereof.

DETAILED DESCRIPTION OF THE DISCLOSURE

The handling of a low dose of a non-bile FXR agonist, such as 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, as disclosed herein, proved difficult. For example, difficulties in weighting the low amount of non-bile FXR agonist and also content uniformity, formulation, dissolution rate and bioavailability issues. Ultimately, those issues were affecting the manufacturing process of the pharmaceutical composition.

Surprisingly, it was found that those challenges can be overcome by mixing a non-bile FXR agonist, such as 2-[(1R,3R,5S)-3-({5-cyclopropyl-3-[2-(trifluoromethoxy)phenyl]-1,2-oxazol-4-yl}methoxy)-8-azabicyclo [3.2.1]octan-8-yl]-4-fluoro-1,3-benzothiazole-6-carboxylic acid, or a pharmaceutically acceptable salt thereof, with at least one lipid excipient. Therefore, the present disclosure reports a new pharmaceutical composition comprising a non-bile farnesoid X receptor (FXR) agonist at a low dose and at least one lipid excipient.

According to the present disclosure, the non-bile FXR agonist of the pharmaceutical composition is 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, referred to herein as Compound A, of formula:

Compound A was disclosed for the first time in WO 2012/087519 (Example 1, compound 1-IB of the table, on page 125) and it is also known under the International Nonproprietary Name (INN) "Tropifexor".

According to the present disclosure, 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, can also be present in its free form. Compound A, as described herein, may also be present in different crystalline forms or in an amorphous state.

Pharmaceutical compositions using conventional suitable pharmaceutical excipients, carriers, or vehicles, proved challenging. Surprisingly, it was found that it was possible to overcome the herein disclosed challenges with a pharmaceutical composition comprising the highly potent Compound A of the present disclosure, and at least one lipid excipient. Lipid excipients and other non-active ingredients suitable for the preparation of the pharmaceutical composition, as disclosed herein, can provide a lipid delivery system. The lipid delivery system can be selected from the Lipid Formulation Classification System (LFCS) developed by C. W. Pouton (Pouton *European Journal of Pharmaceutical Sciences* 11 suppl. 2, 2000, S93-S98; Pouton *Eur. J. Pharm. Sci.* 2006, 29, 278-287; Pouton et al. *Advanced Drug Delivery Reviews*, 2008, 60, 625-637). According to the Lipid Formulation Classification System (LFCS), the lipid delivery systems can be classified into four main groups, so called Type I, Type II, Type III (divided into Type IIIA or Type IIIB), or Type IV.

The "Type I lipid delivery system" or "Type I", according to Pouton's classification, refers to a lipid delivery system which comprises at least one lipid excipient selected from propylene glycol esters of fatty acids, triglycerides and/or mixed glycerides, or mixtures thereof, and no surfactants. The "Type II lipid delivery system" or "Type II" according to Pouton's classification, refers to a self-emulsifying lipid delivery system with a particle size of between 100 to 250 nm, comprising water-insoluble components. Specifically, according to the LFCS classification, the typical Type II lipid delivery system refers to a mixture of between 40 to 80% of at least one lipid excipient selected from propylene glycol esters of fatty acids, triglycerides and/or mixed glycerides, or mixtures thereof, and between 20 to 60% of a water insoluble surfactant with a hydrophilic-lipophilic balance (HLB) inferior at 12 (HLB <12). The "Type III lipid delivery system" or "Type III" according to the LFCS classification refers to self-emulsifying formulations comprising at least one lipid excipient selected from propylene glycol esters of fatty acids, triglycerides and/or mixed glycerides, or mixtures thereof, as disclosed herein, and at least one surfactant with a hydrophilic-lipophilic balance superior at 12 (HLB >12), and optionally a water-soluble co-solvent. Type III lipid delivery system has been referred to as "self-micro-emulsifying" drug delivery system (SMEDDS) to emphasize the very fine emulsion, typically with a particle size of between 100 to 250 nm for Type IIIA and between 50 to 100 nm for Type IIIB. Specifically, Type IIIA lipid delivery system comprises between 40 to 80% of lipid excipient selected from propylene glycol esters of fatty acids, triglycerides and/or mixed glycerides, or mixtures thereof, and between 20 to 40% of water soluble surfactants (HLB >12), and between 0 to 40% of hydrophilic co-solvents. Type IIIB lipid system typically comprises less than 20% of lipid excipient selected from propylene glycol esters of fatty acids, triglycerides and/or mixed glycerides, or mixtures thereof, and between 20 to 50% of surfactants (HLB >12), and between 20 to 50% of hydrophilic co-solvents.

In an aspect, the present disclosure provides for the preparation of a pharmaceutical composition comprising a non-bile FXR agonist, such as Compound A, as disclosed herein, and at least one lipid excipient selected from propylene glycol esters of fatty acids, triglycerides or mixed glycerides, or mixtures thereof.

Propylene glycol esters of fatty acids are propylene glycol mono- and di-esters of fats and fatty acids, which are part of the fatty acyls class of lipids, which encompasses all fatty esters. Propylene glycol esters of fatty acids can be, for example, any fatty acyls that a skilled person in the art would select based on the LIPID MAPS (Fahy et al. *Journal of Lipid Research* 2005, 46, 839-862; Fahy et al. *Journal of Lipid Research* 2009, S9-S14). Propylene glycol esters of fatty acids can be, for example, but not limited to, selected from propylene glycol monoricinoleate, propylene glycol monolaurate, propylene glycol dilaurate, propylene glycol dipelargonate, propylene glycol monocaprylate, propylene glycol dicaprylate/dicaprate, or mixtures thereof.

Triglycerides and/or mixed glycerides are part of the glycerolipid class of lipids, which encompasses all glycerol-containing lipids. Triglycerides and/or mixed glycerides can be, for example, any glycerolipids that a skilled person in the art would select based on the LIPID MAPS. Triglycerides and/or mixed glycerides can be, for example, but not limited to, selected from monoglycerides (short, medium or long chain), diglycerides (short, medium or long chain), triglycerides (short, medium or long chain); more specifically triglycerides and mixed glycerides can be selected from, but not limited to, soybean oil, vegetable oil, corn oil, olive oil, peanut oil, sesame oil, glyceryl tricaprylate/caprate (coconut oil), glyceryl ricinoleate (castor oil), glycerol mono/dicaprylate, glyceryl caprylate/caprate, caprylic/capric triglyceride, or mixtures thereof.

According to the present disclosure, the pharmaceutical composition comprises a non-bile FXR agonist, such as Compound A, and at least one lipid excipient (also called hereafter Type I lipid delivery system). The lipid excipient can be selected from propylene glycol esters of fatty acids, triglycerides and/or mixed glycerides, as described herein, or mixtures thereof. The lipid excipient can be selected from glycerol mono/dicaprylate, glyceryl caprylate/caprate, propylene glycol monolaurate, or mixtures thereof. Specifically, the lipid excipient is at least one excipient selected from glyceryl caprylate/caprate, propylene glycol monolaurate, or mixtures thereof.

According to the present disclosure, the pharmaceutical composition comprises Compound A as herein defined, in an amount of about 0.001% to about 0.04% by weight of the composition, in an amount of about 0.002% to about 0.04% by weight of the composition, or in an amount of about 0.005% to about 0.035% by weight of the composition, and at least one lipid excipient (also called hereafter Type I lipid delivery system). The lipid excipient can be selected from propylene glycol esters of fatty acids, triglycerides and/or mixed glycerides, as described herein, or mixtures thereof. The lipid excipient can be selected from glycerol mono/dicaprylate, glyceryl caprylate/caprate, propylene glycol monolaurate, or mixtures thereof. Specifically, the lipid excipient is at least one excipient selected from glyceryl caprylate/caprate, propylene glycol monolaurate, or mixtures thereof.

According to the present disclosure, the pharmaceutical composition comprises Compound A, as herein defined, in an amount of about 0.005% to about 0.035% by weight of the composition, and at least one lipid excipient (also called hereafter Type I lipid delivery system). Specifically, the lipid excipient is at least one excipient selected from glyceryl caprylate/caprate, propylene glycol monolaurate, or mixtures thereof, and the lipid excipient is in an amount of about 99.998% to about 99.96% by weight of the composition, or in an amount of about 99.995% to about 99.965% by weight of the composition.

When the pharmaceutical composition as disclosed herein comprises mixture of the lipid excipients disclosed herein, then the mixture is present in an amount of about 99.998% to about 99.96% by weight of the composition, or in an amount of about 99.995% to about 99.965% by weight of the composition.

Another aspect of the present disclosure provides for the preparation of a pharmaceutical composition comprising a non-bile FXR agonist, for example Compound A, as disclosed herein, at least one lipid excipient and a surfactant with an HLB <12 (also called hereafter Type II delivery system). More specifically, according to the present disclosure, the Type II lipid delivery system comprises at least one lipid excipient selected from propylene glycol esters of fatty acids, triglycerides and/or mixed glycerides, or mixtures thereof, and at least one surfactant with an HLB <12. The lipid excipient can be any propylene glycol esters of fatty acids, triglycerides and/or mixed glycerides, or mixtures thereof, as disclosed herein. The surfactants, with an HLB <12, that can be used in a Type II lipid delivery system, are, for example, any surfactants selected from, but not limited to, polyoxyethylene (25)-glyceryl trioleate, polyoxyethylene (20) glyceryl trioleate, polyoxyethylene (20) sorbitan trioleate (polysorbate 85), sorbitan fatty acid esters, caprylic/capric triglyceride, or a mixtures thereof. The preferred surfactant that can be used in the Type II lipid delivery system, according to the present disclosure, is at least one surfactant with a HLB <12 selected from polyoxyethylene (25)-glyceryl trioleate, polyoxyethylene (20) glyceryl trioleate, polyoxyethylene (20) sorbitan trioleate, caprylic/capric triglyceride, or mixtures thereof.

According to the present disclosure, the Type II delivery system of the present pharmaceutical composition comprises at least one lipid excipient and at least one surfactant, preferably in a ratio from 20:80 to 40:60. Preferably in a ratio of 25:75 or 50:50. The Type II lipid delivery system can be, for example, but not limited to, propylene glycol monolaurate:caprylic/capric triglyceride, glyceryl caprylate/caprate:caprylic/capric triglyceride, caprylic/capric triglyceride:glycerol mono-/dicaprylate, caprylic/capric triglyceride:polyoxyethylene (25)-glyceryl trioleate, mixture of caprylic/capric triglyceride:glycerol mono-/dicaprylate, or mixtures of caprylic/capric triglyceride with oils:polyoxyethylene (20) sorbitan trioleate. The preferred Type II lipid delivery system is propylene glycol monolaurate:caprylic/capric triglyceride, and glyceryl caprylate/caprate:caprylic/capric triglyceride.

According to the present disclosure, the pharmaceutical composition comprises Compound A as herein defined in an amount of about 0.001% to about 0.04% by weight of the composition, in an amount of about 0.002% to about 0.04% by weight of the composition, or in an amount of about 0.005% to about 0.035% by weight of the composition, and further comprises at least one lipid excipient and at least one surfactant, preferably in a ratio lipid excipient: surfactant from 20:80 to 40:60, preferably in a ratio of 25:75 or 50:50 (also called a Type II delivery system. The Type II lipid delivery system can be, for example, but not limited to, propylene glycol monolaurate:caprylic/capric triglyceride, glyceryl caprylate/caprate:caprylic/capric triglyceride, caprylic/capric triglyceride:glycerol mono-/dicaprylate, caprylic/capric triglyceride:polyoxyethylene (25)-glyceryl trioleate, mixture of caprylic/capric triglyceride:glycerol mono-/dicaprylate, or mixtures of caprylic/capric triglyceride with oils:polyoxyethylene (20) sorbitan trioleate. The preferred Type II lipid delivery system is propylene glycol monolaurate:caprylic/capric triglyceride, and glyceryl caprylate/caprate:caprylic/capric triglyceride.

According to the present disclosure, the pharmaceutical composition comprises Compound A as herein defined, in an amount of about 0.001% to about 0.04% by weight of the composition, in an amount of about 0.002% to about 0.04% by weight of the composition, or in an amount of about 0.005% to about 0.035% by weight of the composition, and a Type II delivery system, wherein the Type II lipid delivery system can be propylene glycol monolaurate:caprylic/capric triglyceride, and glyceryl caprylate/caprate:caprylic/capric triglyceride.

Yet another aspect of the disclosure provides for the preparation of a pharmaceutical composition comprising a non-bile FXR agonist, for example Compound A, as disclosed herein, at least one lipid excipient, a surfactant with an HLB >12, and optionally a co-solvent (also called hereafter Type III delivery system). More specifically, according to the present disclosure, the Type III lipid delivery system comprises at least one lipid excipient selected from propylene glycol esters of fatty acids, triglycerides and/or mixed glycerides, or mixtures thereof, a surfactant with an HLB >12, and optionally a co-solvent. The lipid excipient can be any propylene glycol esters of fatty acids, triglycerides and/or mixed glycerides, or mixtures thereof, as disclosed herein. The surfactants with a HLB >12 that can be used in a Type III lipid delivery system, are, for example, any water soluble surfactants selected from, but not limited to, polyoxyl 40 hydrogenated castor oil, polyoxyl 60 hydrogenated castor oil, alkyl ether ethoxylate, cetostearyl alcohol ethoxylate, polyethylene glycosylated mixed glycerides, macrogolglycerol ricinoleate, polysorbates, sorbitan trioleate, or mixtures thereof. The preferred surfactant, with a HLB >12, suitable for a Type III lipid delivery system according to the present disclosure, is selected from macrogolglycerol ricinoleate, polysorbates, or mixtures thereof. The Type III lipid formulation system may optionally comprise a co-solvent that can be selected from, but is not limited to, ethanol, glycerol, polyethylene glycol, glycofurol, transcutol, propylene glycol, or mixtures thereof.

According to the present disclosure, the Type III lipid delivery system of the present disclosure comprises at least one lipid excipient, a surfactant (HLB >12), and no co-solvent, preferably in a ratio from 20:80 to 40:60. More preferably in a ratio of 25:75 or of 50:50. The Type III lipid delivery system can be, for example, macrogolglycerol ricinoleate:propylene glycol monolaurate, macrogolglycerol ricinoleate:glyceryl caprylate/caprate, polysorbates:propylene glycol monolaurate, polysorbates:glyceryl caprylate/caprate.

The pharmaceutical composition for oral administration, as disclosed herein, is useful, for example, as a medicine for the treatment of an FXR mediated condition or disorder such as, for example, cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis or liver fibrosis. Specifically, the present disclosure provides the use of said pharmaceutical composition in the treatment of primary biliary cirrhosis (PBS) or non-alcoholic steatohepatitis (NASH).

The pharmaceutical composition, as disclosed herein, is intended to be administered orally to humans and animals in unit dosage forms, or multiple-dosage forms, such as, for example, a capsule, a liquid solution, a chewable lozenge, a sterile liquid solution, a liquid suspension, an oral solution or suspension, an oil-water emulsion. Preferably, the pharmaceutical composition, as disclosed herein, is in the form of a liquid solution, or a capsule. More preferably, in the form of a capsule. The pharmaceutical composition, as disclosed herein, can be achieved by mixing the low amount of a non-bile FXR agonist, such as Compound A, with at least one lipid excipient, as disclosed herein. Capsules can be prepared by using techniques known in the art. Suitable capsules can be selected from hard shell capsule, hard gelatin capsule, soft shell capsule, soft gelatin capsule, plant-based shell capsule, or mixtures thereof. The pharmaceutical composition, as described herein, can be presented in a hard gelatin capsule wherein the pharmaceutical composition is further mixed with an inert solid diluent, for example, calcium carbonate, calcium phosphate, or cellulose-based excipient. The pharmaceutical composition, as disclosed herein, can be presented in a gelatin capsule, or a plant-based shell capsule, preferably the capsule is a soft gelatin capsule. The soft gelatin capsule or "softgel capsule" refers to a liquid or a semi-solid matrix inside a one-piece outer gelatin shell. The shell may comprise vegetal or animal gelatin (e.g. pork, beef, or fish based gelatin), water, one or more plasticizers, and possibly some preservatives. The non-bile FXR agonist, such as Compound A, may be either in solution or in suspension in the capsule fill matrix. The shell may be transparent, or opaque, or colored, or flavored. The soft gelatin capsule can be coated by techniques well known in the art with enteric-resistant or delayed-release coating materials, to achieve, for example, greater stability in the gastrointestinal tract, or to achieve the desired rate of release. Soft gelatin capsules of any shape can be prepared (e.g. oval, oblong, twist-off, round, tube, fish, or other suitable shape) and any size (e.g. size 0 to 120) The pharmaceutical composition, as disclosed herein, can also be prepared in the form of a liquid solution.

The non-bile FXR agonist, such as Compound A, as disclosed herein, is present in the pharmaceutical composition in an amount sufficient to exert a therapeutically useful effect in the absence of undesirable side effects on the patient treated. Due to the high potency of Compound A, a low dose is preferable. Each unit dose contain a predetermined amount of the Compound A and at least one lipid excipient, sufficient to produce the desired therapeutic effect. Each unit dose, as disclosed herein, are suitable for human and animal subjects, packaged individually and may be administered in fractions or multiples thereof. A multiple-dose form is a plurality of identical unit-dosage forms packaged in a single container to be administered in segregated unit-dose form. Examples of multiple-dose forms include vials, or bottles.

In accordance with the present disclosure, a non-bile FXR agonist, such as Compound A, may be present in the pharmaceutical composition for oral administration, e.g. capsule, in a low amount. Preferably, Compound A is present in the capsule in an amount between about 1 to 250 µg, about 1 to 120 µg. More preferably, the low amount of the non-bile FXR agonist, such as Compound A, in the capsule is about 1 µg, about 5 µg, about 7 µg, about 10 µg, about 30 µg, about 50 µg, about 60 µg, about 90 µg, about 120 µg, about 140 µg, about 150 µg, about 200 µg, about 210 µg, about 220 µg, about 230 µg, about 240 µg or about 250 µg. More particularly, the amount is about 10 µg, or is about 30 µg, or is about 90 µg, the amount is about 120 µg, the amount is about 140 µg, the amount is about 200 µg, or the amount is about 240 µg. The pharmaceutical composition for oral administration, as disclosed herein, can comprise a mixture of 1 µg of Compound A with at least one lipid excipient. The pharmaceutical composition can also comprise a mixture of 5 µg of Compound A, with at least one lipid excipient. In another example, the pharmaceutical composition for oral administration can also be prepared with 7 µg of Compound A and at least one lipid excipient. The pharmaceutical composition can also comprise, for example, 10 µg of Compound A mixed with at least one lipid excipient, as disclosed herein. In another example, the pharmaceutical composition is prepared by mixing together 30 µg of Compound A, as disclosed herein, and at least one lipid excipient. The pharmaceutical composition can also be prepare with 50 µg of the non-bile FXR agonist, such as Compound A, as disclosed herein, and at least one lipid excipient. The pharmaceutical composition can also be prepared by mixing 60 µg of the non-bile FXR agonist as disclosed herein, with at least one lipid excipient. The pharmaceutical composition can also be prepared by mixing 90 µg of Compound A with at least one lipid excipient. Yet in another example, the pharmaceutical composition can comprise 120 µg of Compound A, as disclosed herein, mixed with at least one lipid excipient. Yet in another example, the pharmaceutical composition can comprise 140 µg of Compound A, as disclosed herein, mixed with at least one lipid excipient. Yet in another example, the pharmaceutical composition can comprise 150 µg of Compound A, as disclosed herein, mixed with at least one lipid excipient. Yet in another example, the pharmaceutical composition can comprise 200 µg of Compound A, as disclosed herein, mixed with at least one lipid excipient. Yet in another example, the pharmaceutical composition can comprise 210 µg of Compound A, as disclosed herein, mixed with at least one lipid excipient. Yet in another example, the pharmaceutical composition can comprise 220 µg of Compound A, as disclosed herein, mixed with at least one lipid excipient. Yet in another example, the pharmaceutical composition can comprise 230 µg of Compound A, as disclosed herein, mixed with at least one lipid excipient. Yet in another example, the pharmaceutical composition can comprise 240 µg of Compound A, as disclosed herein, mixed with at least one lipid excipient. Yet in another example, the pharmaceutical composition can comprise 250 µg of Compound A, as disclosed herein, mixed with at least one lipid excipient.

A further aspect of the present disclosure provides a process for preparing the pharmaceutical composition, as described herein, comprising mixing together a non-bile FXR agonist, such as Compound A, and at least one lipid excipient, and optionally further dissolving, dispersing, or otherwise mixing it with pharmaceutical additives (e.g. adjuvants), such as, by way of example, and without limitation, water, saline, aqueous dextrose, glycerol, glycols, ethanol, beta carotene, alpha tocopherol, butylated hydroxytoluene (BHT), butylated hydroxyanisole (BHA), and the like, to thereby form a liquid mixture, or suspension, or a semi-liquid mixture. The form of the pharmaceutical composition is also dependent of the temperature. For example, the pharmaceutical composition is in a form of a liquid mixture at a temperature between about 2 to about 20° C., preferably between about 2 to about 15° C.

In another aspect, the present disclosure also provides a process for preparing unit dosage form for oral administration using said liquid mixture, or suspension, or semi-liquid mixture, comprising the mixture of a non-bile FXR agonist, for example Compound A, and at least one lipid excipient, as disclosed herein, for example, to prepare a liquid solution. In another example, the liquid or semi-liquid mixture of the pharmaceutical composition, as described herein, can be encapsulated into a hard shell capsule, hard gelatin capsule, soft shell capsule, soft gelatin capsule, plant-based shell capsule, a chewable soft gelatin capsule, a suckable gelatin capsule, a twist-off soft gelatin capsule, or a meltable soft gelatin capsule, or a mixture thereof. Most preferably, the liquid, or semi-liquid mixture is encapsulated into a soft gelatin capsule.

According to the present disclosure, the process for preparing the unit dosage form for oral administration, comprises the steps of:
  i. Mixing a low dose of a non-bile FXR agonist, such as Compound A, with
  ii. a Type I delivery system comprising at least one lipid excipient; or with
    a Type II delivery system comprising at least one lipid excipient and a surfactant with a HLB <12; or with
    a Type III delivery system comprising at least one lipid excipient, a surfactant with a HLB >12, and optionally a co-solvent;
  iii. to obtain a liquid, or a semi-liquid, or a suspended mixture that can be used to prepare an oral solution, or a capsule for oral administration, preferably a soft gelatin capsule,
preferably wherein the non-bile FXR agonist, such as Compound A, is present in an amount between about 1 to about 250 µg, particularly in an amount of about 1 µg, about 5 µg, about 7 µg, about 10 µg, about 30 µg, about 50 µg, about 60 µg, about 90 µg, about 120 µg, about 140 µg, about 150 µg, about 200 µg, about 210 µg, about 220 µg, about 230 µg, about 240 µg, or about 250 µg.

Another aspect of the disclosure also provides the process for preparing the unit dosage form for oral administration, comprising the steps of:
  i. Mixing a low dose of a non-bile FXR agonist, such as Compound A, with a Type I lipid delivery system, and wherein the at least one lipid excipient is, preferably, propylene glycol monolaurate, or glyceryl caprylate/caprate, or mixtures thereof.

ii. to obtain a liquid, or a semi-liquid, or a suspended mixture that can be used to prepare an oral solution or a capsule for oral administration, preferably a soft gelatin capsule, preferably wherein the non-bile FXR agonist, such as Compound A, is present in an amount between about 1 to about 250 μg, particularly in an amount of about 1 μg, about 5 μg, about 7 μg, about 10 μg, about 30 μg, about 50 μg, about 60 μg, about 90 μg, about 120 μg, about 140 μg, about 150 μg, about 200 μg, about 210 μg, about 220 μg, about 230 μg, about 240 μg, or about 250 μg.

Another aspect of the disclosure also provides for the use of the pharmaceutical composition, as disclosed herein, for the manufacture of a medicament for the treatment of an FXR mediated condition or disorder, such as cholestasis, intrahepatic cholestatis, estrogen-induced cholestasis, drug-induced cholestasis, cholestasis of pregnancy, parenteral nutrition-associated cholestasis, primary biliary cirrhosis (PBC), non-alcoholic fatty liver disease (NAFLD), non-alcoholic steatohepatitis (NASH), liver cirrhosis, alcohol-induced cirrhosis, cystic fibrosis or liver fibrosis, preferably for primary biliary cirrhosis (PBS) or non-alcoholic steatohepatitis (NASH), as disclosed herein.

According to the present disclosure, the capsule for oral administration is a soft gelatin capsule, comprising an amount of about 1 μg to about 250 μg of Compound A, and at least one lipid excipient. Preferably, the capsule for oral administration comprises between about 1 μg to about 250 μg of Compound A, as disclosed herein, and at least one lipid excipient. Preferably, the pharmaceutical composition, as disclosed herein, for oral administration comprises Compound A and a Type I lipid delivery system comprising at least one lipid excipient. Preferably, the pharmaceutical composition, as disclosed herein, for oral administration comprises Compound A and a Type II lipid delivery system comprising at least one lipid excipient and a surfactant with an HLB <12. Preferably, the pharmaceutical composition, as disclosed herein, for oral administration comprises Compound A and a Type III lipid delivery system comprising at least one lipid excipient, a surfactant with an HLB >12, and optionally a co-solvent. More preferably, the pharmaceutical composition, as disclosed herein, for oral administration comprises Compound A and a Type I lipid delivery system comprising at least one lipid excipient, wherein the lipid excipient is propylene glycol monolaurate, or glyceryl caprylate/caprate, or mixtures thereof.

Definitions

The term "farnesoid X receptor" or "FXR" refers to all mammalian forms of such receptors including, for example, alternative splice isoforms and naturally occurring isoforms (Huber et al. *Gene* 2002, 290, 35). Representative farsenoid X receptor species include, without limitation, the rat (GenBank Accession No. NM_021745), the mouse (GenBank Accession No. NM_009108), and the human (GenBank Accession No. NM_005123) forms of the receptor.

The term "non-bile FXR agonist" refers to an agent that directly binds to and upregulates the activity of non-bile FXRs. Particularly, the term "agonist" refers to an agent that triggers at least one response by binding a non-endogenous ligand to the receptor. The agonist may act directly or indirectly with a second agent that itself modulates the activity of the receptor. The agonist may also act indirectly by modulating the activity of one or more agent(s) that modulate the amount of FXR mRNA or FXR protein in certain cells of a patient.

The term "pharmaceutically acceptable salts" refers to salts that can be formed, for example, as acid addition salts, preferably with organic or inorganic acids. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. The salts of the non-bile FXR agonist of the present disclosure, are preferably pharmaceutically acceptable salts; suitable counter-ions forming pharmaceutically acceptable salts are known in the field. The term "pharmaceutically acceptable" refers to those compounds, materials, compositions, and/or dosage forms which are suitable for use in contact with the tissues of human beings and animals without excessive toxicity, irritation, allergic response, or other problem or complication, commensurate with a reasonable benefit/risk ratio.

The term "treat", "treating", or "treatment" of any disease or disorder refers to ameliorating the disease or disorder (e.g. slowing or arresting or reducing the development of the disease or at least one of the clinical symptoms thereof), to preventing, or delaying the onset, or development, or progression of the disease or disorder. In addition those terms refers to alleviating or ameliorating at least one physical parameter including those which may not be discernible by the patient and also to modulating the disease or disorder, either physically (e.g. stabilization of a discernible symptom), physiologically (e.g. stabilization of a physical parameter), or both.

The terms "low dose", "low dosage strength", or "low amount", as used herein, can be used interchangeably, and refer to a low amount of the active pharmaceutical ingredient ranging from about 1 μg to about 10 mg, preferably to an amount ranging from about 1 μg to about 1 mg, more preferably the amount is ranging from about 1 to about 250 μg, or from about 1 to about 200 μg.

The term "about", as used herein, is intended to provide flexibility to a numerical range endpoint, providing that a given value may be "a little above" or "a little below" the endpoint accounting for variations one might see in the measurements taken among different instruments, samples, and sample preparations. The term usually means within 10%, preferably within 5%, and more preferably within 1% of a given value or range.

The terms "pharmaceutical composition" or "formulation" can be used herein interchangeably, and relate to a physical mixture containing a therapeutic compound to be administered to a mammal, e.g. a human, in order to prevent, treat, or control a particular disease or condition affecting a mammal. The terms also encompass, for example, an intimate physical mixture formed at high temperature and pressure.

The term "oral administration" represents any method of administration in which a therapeutic compound can be administered through the oral route by swallowing, chewing, or sucking an oral dosage form. Such oral dosage forms are traditionally intended to substantially release and/or deliver the active agent in the gastrointestinal tract beyond the mouth and/or buccal cavity.

The term "a therapeutically effective amount" of a compound, as used herein, refers to an amount that will elicit the biological or medical response of a subject, for example, ameliorate symptoms, alleviate conditions, slow or delay disease progression, etc. The term "a therapeutically effective amount" also refers to an amount of the compound that, when administered to a subject, is effective to at least partially alleviate and/or ameliorate a condition, or a disorder, or a disease. The term "effective amount" means the amount of the subject compound that will engender a biological or medical response in a cell, tissue, organs, system, animal or human that is being sought by the researcher, medical doctor or other clinician.

The term "comprising" is used herein in its open ended and non-limiting sense unless otherwise noted. In a more limited embodiment "comprising" can be replaced by "consisting of", which is no longer open-ended. In a most limited version it can include only feature steps, or values as listed in the respective embodiment.

The term "lipid delivery system" refers to any formulation involving oils, for example comprising propylene glycol esters of fatty acids, triglycerides, mixed mono- and di-glycerides, or mixtures thereof; nonionic surfactants; either alone or as mixtures; optionally in combination with hydrophilic co-solvents.

The term "glycerides" refers to esters formed from glycerol and fatty acids. Glycerol has three hydroxyl functional groups, which can be esterified with one, two or three fatty acids to form monoglycerides, diglycerides and triglycerides, respectively. Glycerides can exist in various size, usually defined as short chain, medium chain or long chain. The term "short chain glyceride" usually possess a small fatty acid group, containing between 2 to 5 carbons, attached to the glycerol backbone. The term "medium chain glyceride" usually refers to a fatty acid group containing between 6 to 12 carbons. The term "long chain glyceride" usually refers to a fatty acid group containing 13 or more carbon atoms.

The term "self-emulsifying" or "self-emulsifying drug delivery system (SEDDS)" refers to isotropic mixtures of natural or synthetic oils, solid or liquid surfactants, or alternatively, one or more hydrophilic solvents and co-solvents/surfactants. The combination of a pharmaceutical oil and a surfactant can provide a formulation, which emulsifies and disperses rapidly in the gastrointestinal fluid. Upon mild agitation followed by dilution in aqueous media, these systems can form fine oil-in-water (o/w) emulsions with a droplet size between 100-300 nm, or micro-emulsions (SMEDDS) with a droplet size of less than 50 nm.

The term "excipient", as used herein, refers to a non-active substance that is added alongside the active pharmaceutical ingredient, and is part of the formulation matrix. All lipid excipients, referred herein, are used in qualities suitable for pharmaceutical use and are commercially available under various brand names as indicated in the following examples:
  Glyceryl caprylate/caprate (Ph.Eur., USP-NF, and INCI), is commercially available under the name of Capmul CMC.
  Propylene glycol monolaurate (Ph. Eur., USP-NF, is commercially available under the name Lauroglycol 90 (which contains 90% of monoesters of 012 fatty acids).
  Glycerol mono-/dicaprylate, also known as glyceryl caprylate (INCI), is commercially available under the name of lmwitor 988.

The term "surfactant" or "surface active agent" refers to an organic compound that possess both a hydrophobic hydrocarbon chain lengths between 12-18 carbon atoms and a hydrophilic head. Surfactants are classified as ionic (e.g. anionic or cationic) or non-ionic, according to their characteristic on dissociation. The hydrophilic-lipophilic balance (HLB) of a surfactant measures the degree to which the surfactant is either hydrophilic or lipophilic. It is determine by calculating the different values of the molecule either by using the Griffin's method (Griffin W. C. *Journal of the Society of Cosmetic Chemists* 1949, 1(5), 311-326; Griffin W. C. *Journal of the Society of Cosmetic Chemists* 1954, 5(4), 249-256) or the Davies' method (Davies J. T. "*A quantitative kinetic theory of emulsion type, I. Physical chemistry of the emulsifying agent*", 1957, page 426-438). The HLB value can be used to determine the surfactant properties of the molecule, for example, a lipid soluble molecule has a HLB <10 (water-insoluble) and a water-soluble molecule has a HLB >10. All the surfactants referred herein are used in qualities suitable for pharmaceutical use and are commercially available under various brand names as indicated in the following examples:
Caprylic/capric triglyceride (INCI) is a medium chain triglyceride commercially available under the name of Miglyol 812N or Miglyol 812 neutral oil. It is also referred to in the literature as triglyceride of caprylic and capric acid.
Macrogolglycerol ricinoleate (INN, Ph. Eur) is commercially available under the name Cremophor EL or Cremophor ELP. It is also known in the literature under the name Polyethylene glycol-660-12-hydroxystearate, or Polyoxyl 15 Castor Oil (USP/NF), PEG-35 Castor Oil (INCI).
Polysorbates is commercially available under the name Tween 80. It is also known in the literature under the names Polysorbate 80, PEO(20) sorbitan mono-oleate (INCI, former name Crillet 4 Super).
Polyoxyethylene (20) sorbitan trioleate is commercially available under the name Tween 85.
Polyoxyethylene (25)-glyceryl trioleate is commercially available under the name Tagat-TO.
Polyoxyl 40 hydrogenated castor oil is commercially available under the name cremophor RH40.
Polyoxyl 60 hydrogenated castor oil is commercially available under the name cremophor RH60.
Abbreviations
API Active pharmaceutical ingredient
AUC Area Under the Curve
Cmax Maximum concentration
CSF Clinical Service Form
h hours
INCI International Nomenclature of Cosmetic Ingredients
Kg/g/mg/ng/µg Kilogram/Gram/Milligram/Nanogram/Microgram
LFCS Lipid formulation classification system
ml Milliliters
Ph. Eur. European pharmacopoeia
PK Pharmacokinetic
ppm Parts-per million
RH Relative humidity
SD Standard deviation
SGC Soft gelatin capsule
SIF Simulated intestinal fluid
Tmax Time to peak maximum concentration (Cmax)
USP-NF US pharmacopoeia

EXAMPLES

The following examples illustrate the disclosure and provide support for the disclosure without limiting the scope of the disclosure.

Example 1

Placebo Formulation

First, a design of experiments was conducted according to Pouton's Lipid Formulation Classification System (LFCS), as disclosed herein, to identify the lipid delivery system candidate for providing formulations with good physical stability. To achieve this, the soft gelatin capsule was filled with only the lipid delivery system (LFCS Type I, Type II or Type III lipid delivery system), without Compound A, and the newly formed capsule was observed to make sure the capsule was stable and thus no phase separation observed.

TABLE 1

LFCS Type I lipid delivery system formulations

| | Ingredients | Ratio [%] | Formulation Aspect | Phase Separation |
|---|---|---|---|---|
| F001 | Glyceryl caprylate/caprate | 100 | Colorless | No |
| F002 | Propylene glycol monolaurate | 100 | Colorless | No |

The Type I lipid delivery system formulation comprises at least one lipid excipient, listed as ingredients in the above Table 1, and no surfactant.

TABLE 2

LFCS Type II lipid delivery system formulations

| | Ingredients | Ratio [%] | Formulation Aspect | Phase Separation |
|---|---|---|---|---|
| F101 | Propylene glycol monolaurate: Caprylic/capric triglyceride | 25:75 | Slightly yellow | No |
| F102 | Propylene glycol monolaurate: Caprylic/capric triglyceride | 50:50 | Slightly yellow | No |
| F103 | Glyceryl caprylate/caprate: Caprylic/capric triglyceride | 25:75 | Slightly yellow | No |

The Type II lipid delivery system formulation comprises at least one lipid excipient and a surfactant (with an HLB <12). Type II lipid delivery system formulations were tested by adding a hydrophobic surfactant (caprylic/capric triglyceride) to the lipid excipients tested in Table 1 (see ingredients column in Table 2). Interestingly, the addition of a hydrophobic surfactant (caprylic/capric triglyceride) increased the solubility of the formulations (compare to the Type I formulations in Table 1) and decreased the digestible potential.

TABLE 3

LFCS Type III lipid delivery system formulations

| | Ingredients | Ratio [%] | Formulation Aspect | Phase Separation |
|---|---|---|---|---|
| F201 | Macrogolglycerol ricinoleate: Propylene glycol monolaurate | 50:50 | Slightly yellow | No |
| F202 | Macrogolglycerol ricinoleate: Glyceryl caprylate/caprate | 50:50 | Slightly yellow | No |
| F203 | Macrogolglycerol ricinoleate: Propylene glycol monolaurate | 25:75 | Slightly yellow | No |
| F204 | Macrogolglycerol ricinoleate: Glyceryl caprylate/caprate | 25:75 | Slightly yellow | No |
| F205 | Polysorbates:Propylene glycol monolaurate | 50:50 | Slightly yellow | No |
| F206 | Polysorbates:Glyceryl caprylate/caprate | 50:50 | Slightly yellow | No |
| F207 | Polysorbates:Propylene glycol monolaurate | 25:75 | Slightly yellow | No |
| F208 | Polysorbates:Glyceryl caprylate/caprate | 25:75 | Slightly yellow | No |

The Type III lipid delivery system formulation comprises at least one lipid excipient, a surfactant (with an HLB >12), and optionally a co-solvent. The formulations in Table 3 were prepared by using the lipid excipient tested in Table 1 (e.g. Glyceryl caprylate/caprate and Propylene glycol monolaurate), and mixing it with a hydrophilic surfactant and no co-solvent. Two hydrophilic surfactants were selected to mitigate the risk of incompatibility with Compound A (e.g. macrogolglycerol ricinoleate, or polysorbates).

All the above placebo formulations (depicted in Tables 1 to 3) passed the test of phase separation, proving that they were all stable. All formulations were selected for further in vitro evaluations.

Example 2

Active Formulation Development

The placebo formulations (Example 1) evaluated and described in Tables 1 to 3 were selected to be combined with Compound A. The Compound A was fully soluble in all formulations and no precipitation was observed after 7 days storage at room temperature. Then, the precipitation of Compound A in each formulation was controlled by microscope under dispersion in pH 6.5 buffer at room temperature. No precipitation of Compound A occurred under dispersion after at least 6 hours in all the developed formulations.

Based on these preliminary screening, some formulations were short listed (see Table 4 below) to perform challenge test with a target concentration of 300 ppm for Compound A, and fill stability study. These selected formulations cover all types of formulation prototypes belonging to the lipid classification (LFCS) as seen in Tables 4 to 6.

TABLE 4

Composition of the formulation

| Name | Ingredients | Ratio [%] | LFCS class | Compound A [ppm] |
|---|---|---|---|---|
| F001 | Glyceryl caprylate/caprate | 100 | I | 299 |
| F002 | Propylene glycol monolaurate | 100 | I | 298 |
| F101 | Propylene glycol monolaurate:Caprylic/capric triglyceride | 25:75 | II | 301 |

TABLE 4-continued

Composition of the formulation

| Name | Ingredients | Ratio [%] | LFCS class | Compound A [ppm] |
|---|---|---|---|---|
| F204 | Macrogolglycerol ricinoleate:Glyceryl caprylate/caprate | 25:75 | III | 300 |
| F208 | Polysorbates:Glyceryl caprylate/caprate | 25:75 | III | 299 |

Table 4 presents five fill formulation prototypes fully characterized by challenge tests at 300 ppm concentration of Compound A. Based on these results, the fill formulation prototypes depicted in Table 4, are robust regarding our development strategy as shown in Table 5 below.

The challenges tests are described further below:

Dispersion studies were performed to check the behavior of the formulations under dilution (i.e. absence of precipitation of Compound A). Dispersion study with Compound A formulations were conducted in 0.1N HCl solution, water and Simulated Intestinal Fluid (SIF) buffer. Approximately 5 ml of medium was placed in a vial and about 200 mg of the fill formulation were added to the medium at room temperature. The resulting mixture was vortexed at initial time point and then periodically inverted. Drug precipitation was checked over 24 hours by microscopic observations.

Temperature cycling study was performed to assess, in accelerate condition, the precipitation of Compound A and the formulation phase separation under temperature variation. Approximately 5 g of the selected fill formulations were stored 24 hours at 2-8° C. and 37° C. over, at least 6 days. Samples were visually observed for clarity, particulate matter and phase separation.

Holding time study was performed to check any physical change of formulation aspect over time at room temperature. The selected fill formulations with Compound A were stored at room temperature for at least 7 days. The samples were observed for a minimum of once a day for clarity, drug precipitation and phase separation. This test is indicative of the short term physical stability of the formulation. In future product stabilities studies, the physical aspects of the capsules fill content will be visually checked.

Water challenge test was performed to check the absence of precipitation of Compound A, at the maximum water content that could be present in the fill formulation, during product manufacture and storage (no water is added to the formulation as an ingredient, although the capsule shell can contain up to 8% water, some of which could potentially migrate into the fill formulation). The selected fill formulations were challenged by adding approximately 10% of water to the formulation. Approximately 2.7 g of fill was weighted into a vial and approximately 0.3 g of water was added. The vial was vortexed for 10 seconds and left at ambient conditions to settle over a period of 2 weeks. Visual and microscopic observations were made (drug precipitation, phase separation, physical aspect).

Plasticizer challenge test was performed to check the absence of precipitation of Compound A at the worst-case plasticizer content that could be present in fill formulation due to their ingress from the capsule shell. The selected fill formulations were challenged by adding approximately 3% of plasticizer to the formulation. Approximately 2.9 g of fill was weighted into a vial and approximately 0.1 g of plasticizer was added. Glycerol and polysorbates were evaluated. The vial was vortexed for 10 seconds and left at ambient conditions to settle over a period of 2 weeks. Visual and microscopic observations were made (drug precipitation, phase separation, physical aspect).

Digestion test was performed to check the absence of recrystallization of Compound A after in-vitro digestion of the formulation. Approximately 0.25 g of selected fill formulation was dissolved in 25 ml of SIF (simulated intestinal fluid) formulation respectively.

TABLE 5

Challenge test summary results

|  | F001 | F002 | F101 | F204 | F208 |
|---|---|---|---|---|---|
| Holding study | OK | OK | OK | OK | OK |
| Cycling study | OK | OK | OK | OK | OK |
| Water challenge | OK | OK | OK | OK | OK |
| Plasticizer challenge | OK | OK | OK | OK | OK |
| Dispersion test | OK | OK | OK | OK | OK |
| Digestion study | OK | OK | OK | OK | OK |
| SELECTION | YES | YES | YES | YES | YES |

Two formulations presented in Table 5 were selected based on combination of physico-chemical stability and regulatory status of the excipients. The fill stability study performed on these formulations did not show any trend of degradation after 6 weeks.

Example 3

Dog Study

TABLE 6

Formulation composition tested on dog study

| F002 | F101 |
|---|---|
| 100% Propylene glycol monolaurate | 25% Propylene glycol monolaurate 75% Caprylic/capric triglyceride |

The formulations were evaluated in male beagle dogs (see FIG. 1), at n=4 crossover and treated with pentagastrin 30 minutes before the administration. The dogs were fasted overnight and regular food was provided 4 hours after Compound A was administered. The formulations were dosed in hard gelatin capsule for the CSF and in solution for the formulation variants (solution filled into hard gelatin capsules), all at 0.05 mg per dog. The CSF preparation comprised Compound A, lactose, polyvinyl-polypyrrolidone, and magnesium stearate.

Figure 1:
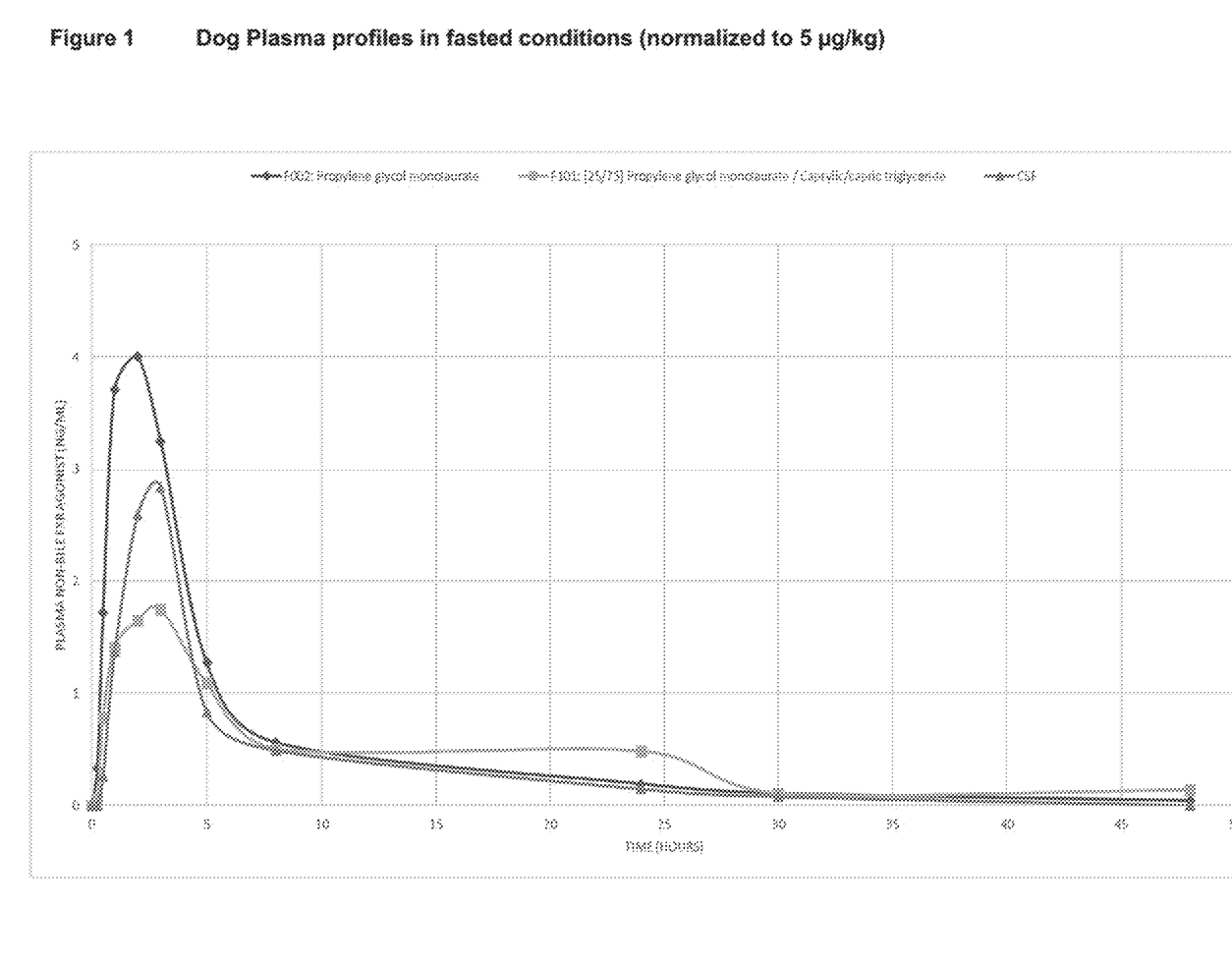
FIG. 1 depicts the dog plasma profile resulting from the administration of the pharmaceutical composition comprising a non-bile FXR agonist, such as 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient, in fasted conditions (normalized to 5 µg/kg).

The pharmacokinetic (PK) profile of the CSF formulation was compared with the selected formulations as described in Table 6 (i.e. F002, F101). The results shows that, the Tmax for the CSF is higher (2.8 hours) than for the formulations (1.8-2.5 hours) and exposure (AUC) is similar for the three lipidic formulations, around 40% better than for the CSF formulation, see Table 7. Formulation F002 containing 100% propylene glycol monolaurate shows 40% higher concentration achieved than the CSF. As seen in FIG. 1, Formulation F002 obtains higher Cmax in a shorter time than all other formulations.

After 6 months, the stability results, as showed in Table 8 and Table 9, confirm the stability of the drug product and no degradations at high temperature is observed. The variation observed between 0 months and 6 months can be explained by the relative low drug load, which makes small variation important.

TABLE 7

Dog PK results

| PK parameters of Compound A | F002 100% Propylene glycol monolaurate [a, b] | F101 Propylene glycol monolaurate/ Caprylic/capric triglyceride [25:75] [a, b] | CSF formulation [b] |
|---|---|---|---|
| Tmax [h] | 1.80 ± 0.50 | 2.30 ± 0.96 | 2.80 ± 0.50 |
| Cmax/Dose [(ng/mL)/(μg/kg)] | 0.73 ± 0.06 | 0.41 ± 0.10 | 0.55 ± 0.10 |
| AUClast/Dose [(ng*h/mL)/(μg/kg)] | 4.41 ± 0.60 | 4.25 ± 1.11 | 3.16 ± 0.62 |
| AUCinf/Dose [(ng*h/mL)/(μg/kg)] | 4.54 ± 0.59 | 4.91 ± 1.69[c] | 3.34 ± 0.65 |
| Cmax ratio | 1.38 ± 0.33 | 0.75 ± 0.20 | Reference |
| AUClast ratio | 1.42 ± 0.23 | 1.36 ± 0.34 | Reference |
| AUCinf ratio | 1.38 ± 0.23 | 1.40 ± 0.31[d] | Reference |

Values are mean ± SD, n = 4
[a] Actual doses were determined using the weight of each filled capsule.
[b] Doses were calculated using the average weight of each dog measured over each study.
[c] There was a fluctuation in exposure for F101 in the terminal phase for one dog (extrapolated AUC was around 28%).
[d] The AUClast, (AUC up to the last measurable concentration) instead of AUCinf (AUC curve up to infinite time), for one of dogs was used since its extrapolated AUC was around 28%.

Figure 2:
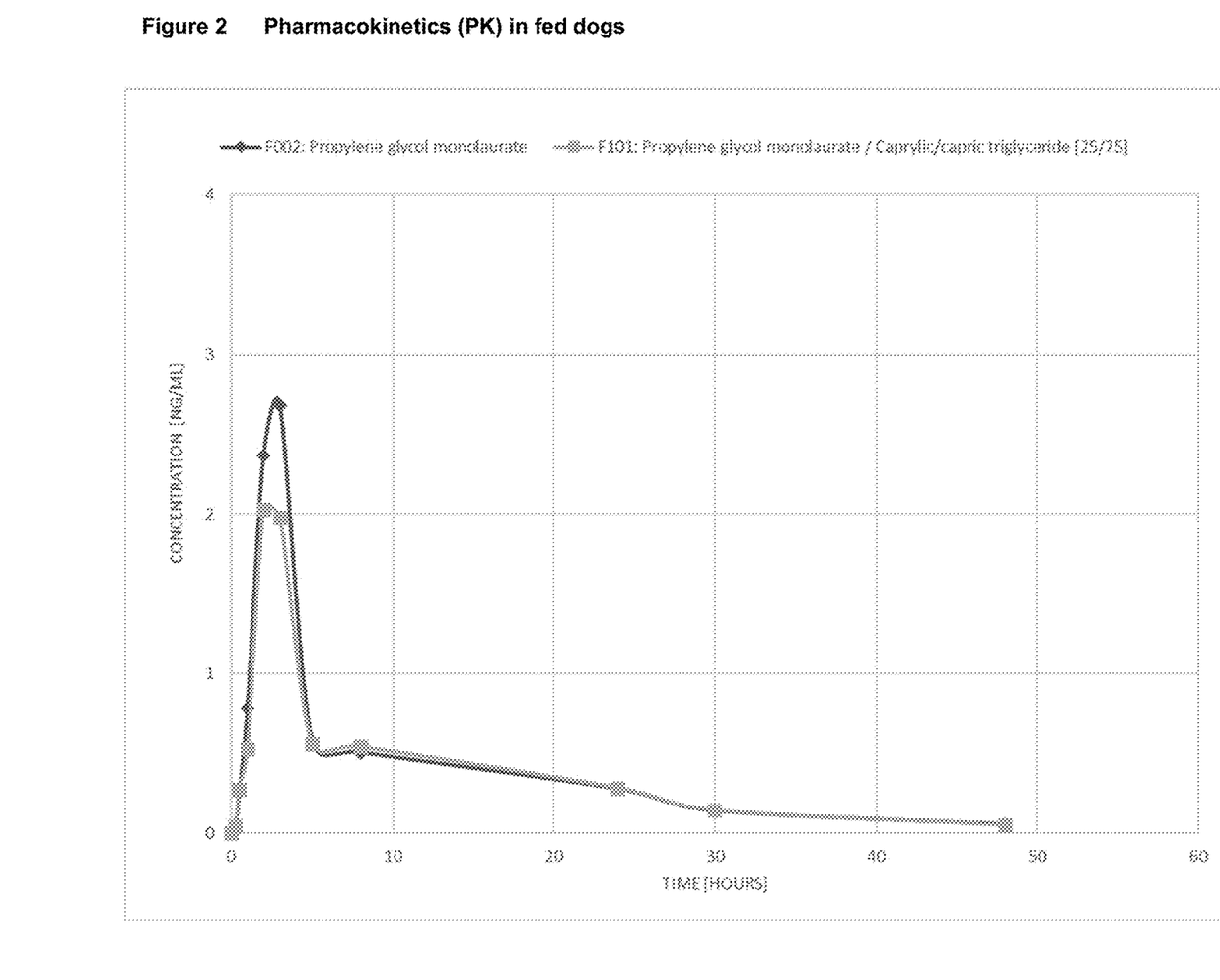
FIG. 2 depicts the pharmacokinetic (PK) profile of the pharmaceutical composition, comprising the non-bile FXR agonist 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid, or a pharmaceutically acceptable salt thereof, and at least one lipid excipient, once administered in fed dogs.

The pharmacokinetic (PK) profile of the pharmaceutical composition was also studied in fed dogs (beagle dogs, male, fasted overnight, crossover n=4) as showed in FIG. 2. The Dogs received a pretreatment of pentagastrin, 30 minutes before Compound A dosing. The targeted dose was 0.05 mg, the volume was divided into 2 soft gelatin capsules. FIG. 2 compares the PK profile in fed condition for the formulation F002 (100% propylene glycol monolaurate) and formulation F101 (25% propylene glycol monolaurate/75% caprylic/capric triglyceride). The PK profile is similar which shows that the propylene glycol monolaurate formulation (F002) presents a positive food effect in comparison to the F101 formulation.

Example 4

Stability Assays for Formulations of Compound A in the Soft Gelatin Capsule

TABLE 8

Assay Stability data formulation F002 of Compound A in the soft gelatin capsule, 0.03 mg in blister

| Time [month] | 0 | 1 | 1.5 | 3 | 6 |
|---|---|---|---|---|---|
| 5° C. | 102.2% | 102.1% | 100.5% | 98.4% | 100.6% |
| 25° C./60% RH | 102.2% | 104.1% | 100.9% | 98.2% | 99.7% |
| 40° C./75% RH | 102.2% | 103.7% | 102.7% | 98.2% | 100.2% |

TABLE 9

Assay Stability data of formulation F102 Compound A in the soft gelatin capsule, 0.09 mg in blister

| Time [month] | 0 | 1 | 1.5 | 3 | 6 |
|---|---|---|---|---|---|
| 5° C. | 103.6% | 104.0% | 101.1% | 98.2% | 101.2% |
| 25° C./60% RH | 103.6% | 103.8% | 103.0% | 98.5% | 101.2% |
| 40° C./75% RH | 103.6% | 103.1% | 96.8% | 99.1% | 101.0% |

Example 5

Formulation of Compound A in the Soft Gelatin Capsule

TABLE 10

Example of formulation with propylene glycol monolaurate and different amounts of Compound A.

| Formulations | 1 | 2 | 3 | 4 |
|---|---|---|---|---|
| Compound A | 30 μg | 90 μg | 140 μg | 200 μg |
| 100% Propylene glycol monolaurate | 139.97 mg | 263.91 mg | 409.86 mg | 585.80 mg |
| Total fill weight/capsule | 140.0 mg | 264.0 mg | 410.0 mg | 586.0 mg |

Table 10 presents four fill formulation prototypes containing different amounts of Compound A with 100% propylene glycol monolaurate.

TABLE 11

Example of formulation with propylene glycol monolaurate and caprylic/capric triglyceride with different amounts of Compound A.

| Formulations | 1 | 2 |
|---|---|---|
| Compound A | 10 μg | 200 μg |
| Propylene glycol monolaurate | 35.00 mg | 146.45 mg |
| caprylic/capric triglyceride | 104.99 mg | 439.35 mg |

Table 11 presents four fill formulation prototypes containing different amounts of Compound A with propylene glycol monolaurate and caprylic/capric triglyceride.

The invention claimed is:
1. A pharmaceutical composition comprising: (i) about 0.001% to about 0.04% by weight of said composition of

2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof; and (ii) propylene glycol monolaurate; wherein said composition optionally comprises a surfactant.

2. The pharmaceutical composition according to claim 1, comprising (i) about 0.001% to about 0.04% by weight of said composition of 2[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof; and (ii) propylene glycol monolaurate in an amount of about 99.96% by weight of said composition.

3. The pharmaceutical composition according to claim 2, comprising about 0.002 to about 0.04% by weight of said composition of 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof.

4. The pharmaceutical composition according to claim 2, comprising about 0.005 to about 0.035% by weight of said composition of 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid or a pharmaceutically acceptable salt thereof.

5. The pharmaceutical composition according to claim 1, wherein said composition further comprises a surfactant and the ratio of said propylene glycol monolaurate to said surfactant is about 25:75.

6. The pharmaceutical composition according to claim 1, wherein said composition further comprises a surfactant and the ratio of said propylene glycol monolaurate to said surfactant is about 50:50.

7. The pharmaceutical composition of claim 1, wherein said surfactant comprises caprylic/capric triglyceride.

8. The pharmaceutical composition of claim 1, wherein said composition is a liquid solution.

9. The pharmaceutical composition of claim 1, wherein said composition is a capsule.

10. The pharmaceutical composition of claim 9, wherein said capsule is a gelatin capsule.

* * * * *